(12) United States Patent
DiUbaldi et al.

(10) Patent No.: US 8,588,930 B2
(45) Date of Patent: Nov. 19, 2013

(54) PIEZOELECTRIC STIMULATION DEVICE

(75) Inventors: Anthony DiUbaldi, Jackson, NJ (US);
Stephen Wahlgren, Easton, PA (US);
Michael R. Tracey, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 775 days.

(21) Appl. No.: 12/661,949

(22) Filed: Mar. 26, 2010

(65) Prior Publication Data

US 2010/0249677 A1    Sep. 30, 2010

Related U.S. Application Data

(63) Continuation-in-part of application No. 11/146,522, filed on Jun. 7, 2005, now Pat. No. 7,979,137.

(60) Provisional application No. 61/211,197, filed on Mar. 27, 2009.

(51) Int. Cl.
*A61N 1/36*    (2006.01)

(52) U.S. Cl.
USPC .......................................................... 607/71

(58) Field of Classification Search
USPC ..................................... 607/41, 71
See application file for complete search history.

(56) References Cited

U.S. PATENT DOCUMENTS

| | | | |
|---|---|---|---|
| 3,683,915 A | 8/1972 | Voss | |
| 3,902,502 A | 9/1975 | Liss et al. | |
| 3,933,147 A | 1/1976 | DuVall et al. | |
| 3,941,136 A | 3/1976 | Bucalo | |
| 4,406,288 A | 9/1983 | Horwinski et al. | |
| 4,537,195 A | 8/1985 | McDonnell | |
| 4,719,922 A | 1/1988 | Padjen et al. | |
| 4,909,255 A | 3/1990 | Farin | |
| 4,989,605 A | 2/1991 | Rossen | |
| 5,167,237 A | 12/1992 | Rabin et al. | |
| 5,350,414 A | 9/1994 | Kolen | |
| 5,358,514 A | 10/1994 | Schulman | |
| 5,421,817 A | 6/1995 | Liss et al. | |
| 5,458,630 A | 10/1995 | Hoegnelid et al. | |

(Continued)

FOREIGN PATENT DOCUMENTS

| | | |
|---|---|---|
| CN | 1593683 | 3/2005 |
| CN | 1745857 | 3/2006 |

(Continued)

OTHER PUBLICATIONS

Reilly, J. Patrick, "Electrical Stimulation and Electropathology," Cambridge University Press (1992); pp. 120-129; 190-205; 252-261; 308-325; 447-459.

(Continued)

*Primary Examiner* — Luther Behringer
(74) *Attorney, Agent, or Firm* — Cheryl F. Cohen, LLC (57) ABSTRACT

A method for stimulating a predetermined body part such as a nerve using a stimulation device including an external non-implantable transmitting device powered by a power source and generating an electrical waveform signal. A surface electrode applies the generated electrical waveform signal transcutaneously. An implantable piezoelectric element receives the applied electrical waveform signal generated transcutaneously and, in turn, causes mechanical deformation resulting in mechanical vibration of the implantable piezoelectric element sufficient to stimulate the predetermined body part. The electrical waveform signal may be either a high frequency continuous waveform or high frequency burst packets.

21 Claims, 4 Drawing Sheets

(56) References Cited

U.S. PATENT DOCUMENTS

| | | |
|---|---|---|
| 5,464,434 A | 11/1995 | Alt |
| 5,476,481 A | 12/1995 | Schondorf |
| 5,487,759 A | 1/1996 | Bastyr et al. |
| 5,556,421 A | 9/1996 | Prutchi et al. |
| 5,558,640 A | 9/1996 | Pfeiler et al. |
| 5,562,717 A | 10/1996 | Tippey et al. |
| 5,617,876 A | 4/1997 | van Duyl |
| 5,645,062 A | 7/1997 | Anderson et al. |
| 5,702,428 A | 12/1997 | Tippey et al. |
| 5,722,996 A | 3/1998 | Bonnet et al. |
| 5,730,125 A | 3/1998 | Prutchi et al. |
| 5,735,887 A | 4/1998 | Barreras, Sr. et al. |
| 5,791,344 A | 8/1998 | Schulman et al. |
| 5,851,223 A | 12/1998 | Liss et al. |
| 5,902,329 A | 5/1999 | Hoffmann et al. |
| 5,984,854 A | 11/1999 | Ishikawa et al. |
| 5,993,414 A | 11/1999 | Haller |
| 6,035,236 A | 3/2000 | Jarding et al. |
| 6,092,530 A | 7/2000 | Weissman et al. |
| 6,099,479 A | 8/2000 | Christopherson et al. |
| 6,155,267 A | 12/2000 | Nelson |
| 6,164,284 A | 12/2000 | Schulman et al. |
| 6,167,304 A | 12/2000 | Loos |
| 6,183,461 B1 | 2/2001 | Matsuura et al. |
| 6,199,575 B1 | 3/2001 | Widner |
| 6,205,359 B1 | 3/2001 | Boveja |
| 6,221,024 B1 | 4/2001 | Miesel |
| 6,231,516 B1 | 5/2001 | Keilman et al. |
| 6,240,317 B1 | 5/2001 | Villaseca et al. |
| 6,263,246 B1 | 7/2001 | Goedeke et al. |
| 6,285,897 B1 | 9/2001 | Kilcoyne et al. |
| 6,298,272 B1 | 10/2001 | Peterfeso et al. |
| 6,330,885 B1 | 12/2001 | Weissman et al. |
| 6,354,991 B1 | 3/2002 | Gross et al. |
| 6,360,129 B1 | 3/2002 | Ley et al. |
| 6,366,814 B1 | 4/2002 | Boveja et al. |
| 6,377,853 B1 | 4/2002 | Malaney et al. |
| 6,384,353 B1 | 5/2002 | Huang et al. |
| 6,402,689 B1 | 6/2002 | Scarantino et al. |
| 6,404,204 B1 | 6/2002 | Farruggia et al. |
| 6,413,393 B1 | 7/2002 | Van Antwerp et al. |
| 6,432,050 B1 | 8/2002 | Porat et al. |
| 6,438,407 B1 | 8/2002 | Ousdigian et al. |
| 6,442,413 B1 | 8/2002 | Silver |
| 6,443,883 B1 | 9/2002 | Ostrow et al. |
| 6,447,462 B1 | 9/2002 | Wallace et al. |
| 6,459,933 B1 | 10/2002 | Lurie et al. |
| 6,471,645 B1 | 10/2002 | Warkentin et al. |
| 6,497,655 B1 | 12/2002 | Linberg et al. |
| 6,505,074 B2 | 1/2003 | Boveja et al. |
| 6,516,227 B1 | 2/2003 | Meadows |
| 6,535,766 B1 | 3/2003 | Thompson et al. |
| 6,560,490 B2 | 5/2003 | Grill et al. |
| 6,567,706 B2 | 5/2003 | Bar-Or et al. |
| 6,652,449 B1 | 11/2003 | Gross et al. |
| 6,662,052 B1 | 12/2003 | Sarwal et al. |
| 6,668,191 B1 | 12/2003 | Boveja |
| 6,701,185 B2 | 3/2004 | Burnett et al. |
| 6,712,772 B2 | 3/2004 | Cohen et al. |
| 6,751,501 B1 | 6/2004 | Schuler et al. |
| 6,836,684 B1 | 12/2004 | Rijkhoff et al. |
| 6,862,480 B2 | 3/2005 | Cohen et al. |
| 6,879,859 B1 | 4/2005 | Boveja |
| 6,907,293 B2 | 6/2005 | Grill et al. |
| 7,047,078 B2 | 5/2006 | Boggs, II et al. |
| 7,054,690 B2 * | 5/2006 | Imran ............... 607/40 |
| 7,062,330 B1 | 6/2006 | Boveja et al. |
| 7,310,557 B2 * | 12/2007 | Maschino et al. ...... 607/40 |
| 7,387,603 B2 | 6/2008 | Gross et al. |
| 7,427,280 B2 | 9/2008 | Gerber |
| 7,502,652 B2 * | 3/2009 | Gaunt et al. ............. 607/46 |
| 7,599,736 B2 | 10/2009 | DiLorenzo |
| 7,676,271 B2 | 3/2010 | Wahlstrand et al. |
| 7,815,895 B2 | 10/2010 | Katagiri et al. |
| 8,170,683 B2 | 5/2012 | Wahlgren |
| 2001/0018606 A1 | 8/2001 | Ingle et al. |
| 2001/0025137 A1 | 9/2001 | Webb et al. |
| 2001/0051768 A1 | 12/2001 | Schulman et al. |
| 2002/0001870 A1 | 1/2002 | Oda et al. |
| 2002/0011592 A1 | 1/2002 | Matsuo |
| 2002/0026141 A1 | 2/2002 | Houben et al. |
| 2002/0026244 A1 | 2/2002 | Trieu |
| 2002/0082480 A1 | 6/2002 | Riff et al. |
| 2002/0103514 A1 | 8/2002 | Abrahamson |
| 2002/0107540 A1 | 8/2002 | Whalen et al. |
| 2002/0111542 A1 | 8/2002 | Warkentin et al. |
| 2002/0133196 A1 | 9/2002 | Thompson |
| 2002/0151816 A1 | 10/2002 | Rich et al. |
| 2003/0004403 A1 | 1/2003 | Drinan et al. |
| 2003/0004553 A1 | 1/2003 | Grill et al. |
| 2003/0162021 A1 | 8/2003 | van Heerden et al. |
| 2003/0204224 A1 | 10/2003 | Torgerson et al. |
| 2003/0212305 A1 | 11/2003 | Anderson et al. |
| 2003/0220669 A1 | 11/2003 | Shealy |
| 2003/0233137 A1 | 12/2003 | Paul |
| 2004/0068203 A1 | 4/2004 | Gellman et al. |
| 2004/0236194 A1 | 11/2004 | Meyer |
| 2005/0177067 A1 | 8/2005 | Tracey et al. |
| 2005/0277998 A1 | 12/2005 | Tracey et al. |
| 2006/0047325 A1 | 3/2006 | Thimineur et al. |
| 2006/0095090 A1 | 5/2006 | De Ridder |
| 2006/0111756 A1 | 5/2006 | Chang |
| 2006/0167500 A1 | 7/2006 | Towe et al. |
| 2006/0178703 A1 | 8/2006 | Huston |
| 2006/0195146 A1 | 8/2006 | Tracey et al. |
| 2006/0195153 A1 | 8/2006 | DiUbaldi |
| 2006/0229688 A1 | 10/2006 | McClure |
| 2006/0247721 A1 | 11/2006 | Maschino |
| 2007/0162085 A1 | 7/2007 | DiLorenzo |
| 2007/0167990 A1 | 7/2007 | Mangrum et al. |
| 2007/0219606 A1 | 9/2007 | Moreci et al. |
| 2007/0233204 A1 | 10/2007 | Lima et al. |
| 2007/0260288 A1 | 11/2007 | Gross |
| 2008/0132962 A1 | 6/2008 | DiUbaldi et al. |
| 2008/0132969 A1 | 6/2008 | Bennett et al. |
| 2008/0147146 A1 | 6/2008 | Wahlgren et al. |
| 2008/0161874 A1 | 7/2008 | Bennett et al. |
| 2008/0293830 A1 | 11/2008 | Katagiri et al. |
| 2009/0005713 A1 | 1/2009 | Podrazhansky et al. |
| 2009/0048642 A1 | 2/2009 | Goroszeniuk |
| 2009/0054952 A1 | 2/2009 | Glukhovsky et al. |
| 2009/0062874 A1 | 3/2009 | Tracey et al. |
| 2009/0132018 A1 | 5/2009 | DiUbaldi et al. |
| 2009/0157149 A1 | 6/2009 | Wahlgren et al. |
| 2009/0187230 A1 | 7/2009 | Dilorenzo |
| 2010/0042018 A1 | 2/2010 | Kleinsinger |
| 2010/0042180 A1 | 2/2010 | Mueller et al. |
| 2010/0076533 A1 | 3/2010 | Dar et al. |

FOREIGN PATENT DOCUMENTS

| | | |
|---|---|---|
| DE | 10033400 | 1/2001 |
| EP | 0783267 | 2/1999 |
| EP | 1048264 | 11/2000 |
| JP | 200316991 | 11/2000 |
| JP | 2001-259047 | 9/2001 |
| JP | 2003135607 | 5/2003 |
| WO | WO 90/14127 | 11/1990 |
| WO | WO 97/18856 | 5/1997 |
| WO | WO 97/39796 | 10/1997 |
| WO | WO 99/55411 | 11/1999 |
| WO | WO 00/33738 | 5/2000 |
| WO | WO 00/33065 | 6/2000 |
| WO | WO 01/49369 | 7/2001 |
| WO | WO 01/56633 | 8/2001 |
| WO | WO 02/22008 | 3/2002 |
| WO | WO 02/27294 | 4/2002 |
| WO | WO 02/058551 | 8/2002 |
| WO | WO 02/062215 | 8/2002 |
| WO | WO 03/015625 | 2/2003 |
| WO | WO 03/020364 | 3/2003 |
| WO | WO 03/030733 | 4/2003 |
| WO | WO 03/071944 | 9/2003 |
| WO | WO 2004/050172 | 6/2004 |

(56) References Cited

FOREIGN PATENT DOCUMENTS

| WO | WO 2005/002663 | 1/2005 |
|---|---|---|
| WO | WO 2005/079909 | 9/2005 |
| WO | WO 2007/092301 A2 | 8/2007 |

OTHER PUBLICATIONS

Copending, co-owned U.S. Appl. No. 60/543,722, filed Feb. 11, 2004.
Copending, co-owned U.S. Appl. No. 11/043,830, filed Jan. 26, 2005.
Copending, co-owned U.S. Appl. No. 11/146,522, filed Jun. 7, 2005.
Copending, co-owned U.S. Appl. No. 11/343,627, filed Jan. 31, 2006.
Copending, co-owned U.S. Appl. No. 12/661,949, filed Mar. 26, 2010.
Copending, co-owned U.S. Appl. No. 11/344,825, filed Jan. 31, 2006.
Copending, co-owned U.S. Appl. No. 13/094,644, filed Apr. 26, 2011.
Copending, co-owned U.S. Appl. No. 61/211,197, filed Mar. 27, 2009.
Beceker, T.J., "Cardio MEMS Moves Closer to Commercializing its Innovative Heart Sensors," (Feb. 27, 2005) ATDC News & Information, Georgia Institute of Technology.
Chappel, J., Electronic News—Ambient Intelligence (2002).
Rousche, P.J. et al., "Flexible Polyimide-Based Intracortical Electrode ARrays with Bioactive Capacity," IEEE Transactions on Biomedical Engineering, vol. 48, No. 3 (2001).
Siwapornsathain, E. et al., "Telemetry and Sensor Platform for Ambulatory Urodynamics," Proceedings 2nd Annual International IEEE-EMBS Special Topica Conference (May 2002).
Voskerician, G. et al., "Biocompatiblity and Biofouling of MEMS Drug Delivery Devices," Biomaterials, 24 (2003), pp. 1959-1967.
Walter, et al., "Evaluation of a 316LVM Woven Eye Electrode for Direct Bladder Stimulation," Engineering in Medicine and Biology Society 1991, vol. 13 (1991), pp. 1853-1854.
Fiber Optic Sensors, Products Datasheet FOP—M Pressure Sensor (undated).
Frost & Sullivan Report (2002).
Rossell, J. et al., "Skin Impedance from 1 Hz to 1 MHz," IEEE Transactions on Biomedical Engineering, vol. 35, No. 8, Aug. 1988.
Reilly, J. Patrick, "Electrical Stimulation and Electropathology," Cambridge University Press (1992).
Junge, et al., "Titanium Coating of a Polypropylene Mesh for Hernia Repair: Effect on Biocompatibility," Hernia, vol. 6, No. 9, pp. 115-119, pub'd on line Dec. 4, 2004.
International Search Report dated Sep. 2, 2010 for International Application No. PCT/US2010/028690 (8 pages).
English translation of Jun. 26, 2012 Office Action from Japanese Patent Office in counterpart Japanese Patent Application No. 2008-515738 (3 pages).
Co-owned, copending U.S. Appl. No. 11/866,588, filed Oct. 3, 2007.

\* cited by examiner

*FIG. 7*

PIEZOELECTRIC STIMULATION DEVICE

CROSS-REFERENCE TO RELATED APPLICATIONS

This application is a continuation-in-part of U.S. patent application Ser. No. 11/146,522, now issued as U.S. Pat. No. 7,979,137, filed on Jun. 7, 2005, which is herein incorporated by reference in its entirety; and claims the benefit of U.S. Provisional Application No. 61/211,197, filed Mar. 27, 2009, which is herein incorporated by reference in its entirety.

BACKGROUND OF THE INVENTION

1. Field of the Invention

The present invention is directed to piezoelectric stimulation of a predetermined body part, e.g., a nerve.

2. Description of Related Art

Nerve and muscle cells have membranes that are composed of lipids and proteins, and have unique properties of excitability such that an adequate disturbance of the cell's resting potential can trigger a sudden change in the membrane conductance. A neuronal process can be divided into unit lengths, which can be represented in an electrical equivalent circuit. Each unit length of the process is a circuit with its own membrane resistance, membrane capacitance and axonal resistance.

A nerve cell can be excited by increasing the electrical charge within the nerve, thus increasing the membrane potential inside the nerve with respect to the surrounding extracellular fluid. This fundamental feature of the nervous system i.e., its ability to generate and conduct electrical impulses, can take the form of action potentials (AP), which are a single electrical impulse passing down an axon. This action potential (nerve impulse or spike) is an "all or nothing" phenomenon. That is, once the threshold stimulus intensity is reached, an action potential will be generated.

Nerve stimulation may be realized by applying electrical pulses having different frequencies, amplitudes and waveforms. Stimulating electrical signals may be generated by electrodes disposed close to the target nerve or tissue of interest. Transcutaneous Electrical Nerve Stimulators (TENS) produce an electrical signal at frequencies up to approximately 200 Hz to stimulate nerves for relatively small periods of time. TENS use a small electrical device to deliver low frequency (10 Hz to 100 Hz) electrical impulses through the skin via electrode pads affixed to the skin. Electrodes are located at selected locations on the patient's skin and the electrical energy is transferred between the two electrodes. Electrical energy is generally applied in the form of low frequency electrical impulses. The impulses pass through the skin and interact with the nerves that lie beneath the skin. A typical TENS device includes a stimulator, lead wires and electrodes attached to the surface of the skin of the patient. The stimulator is an electrical pulse generator that delivers electrical pulses at a predetermined or selectable frequency. TENS devices are only effective in treating nerves very close to the surface of the skin because the low frequency electrical impulses diminish in strength very quickly due to tissue impedance and thus are not sufficient in intensity to stimulate nerves deep beneath the skin. As an alternative to surface electrodes, implantable electrodes may be surgically implanted proximate a target nerve or tissue of interest to be stimulated. The need for invasive surgery makes such implanted electrodes undesirable.

Aside from electrical stimulation, a nerve cell can also be excited by mechanical vibration which increases the membrane potential inside the nerve with respect to the surrounding extracellular fluid. This mechanical vibration or resonance can be detected by nerve endings if above a certain threshold frequency; that is, a minimum threshold level of stimuli is required before the action potential is triggered or fired. If the threshold stimulus intensity is reached an electrical signal is passed along the axon of the nerve and an action potential is fired.

PCT International Publication WO 2005/079909 discloses a method and apparatus for the detection and treatment of respiratory disorders using implanted devices to mechanically stimulate afferent nerves so as to indirectly cause an increase of the tone of upper airway muscles normally involved with maintenance of upper airway patency. The tone of the upper airway muscles typically decrease during Obstructive Sleep Apnea (OBS), contributing to a collapse and obstruction of the airway. During wakefulness reflexes work to maintain tone in upper airway muscles thereby preventing airway collapse. This reflex mechanism is substituted or enhanced during sleep to restore or maintain airway patency by the application of electrical or mechanical stimulation applied to the afferent nerves. In the case of mechanical stimulation a mechanical element, for example, a piezo-electric element, is implanted at a site in the vicinity of the upper airway, for example, within or adjacent to the base of the genioglossus muscle. A controller sends an electrical signal to the piezo-electric element thereby eliciting a vibration. Vibration of the element elicits stimulation of mechanoreceptor afferent nerve endings within the upper airway. The amplitude, frequency and duration of the mechanical stimulation are controlled such that sufficient stimulation of afferent nerves is achieved without sensory stimulation sufficient to cause arousal from sleep. The mechanical stimulation of afferent nerves would typically be achieved by a period of several seconds of vibration at frequencies in the range of 10-50 Hz, and is tuned to the frequency at which the target receptors are most sensitive. As is evident from the required low frequency range stimulus of 10-50 Hz, the electrical signal used to invoke the mechanical vibrations must inherently be produced by an implanted pulse generator. Otherwise, transcutaneous delivery of such a low frequency electrical signal generated by a non-invasive signal generator would not be sufficient in strength or intensity to trigger stimulation of the afferent nerve beneath the skin as most of the energy would be dissipated at the level of the skin. As noted above, such a pulse generator that generates only low frequency would require surgery to be implanted. It is therefore, desirable to develop a piezoelectric neurostimulator implanted in proximity to a nerve of interest and employing a non-invasive signal generator to cause electrical stimulation of the piezo element resulting in mechanical vibration/resonance of the piezo element thereby stimulating the nerve.

U.S. Patent Application Publication No. 2006/0167500 discloses a neurostimulator using an implanted piezo-electric chip as an electrode. The neurostimulator includes driving circuitry connected to an ultrasound transducer and at least one piezoelectric chip located proximate a nerve fiber. The ultrasound transducer is positioned to create a pressure wave that is incident on the piezoelectric chip. The excitation of the piezoelectric materials in the piezoelectric chip generates an electric current that can then be used to stimulate an action potential or inhibit the creation of an action potential in the nerve. Here a mechanical signal is transmitted through the skin and is converted to an electrical signal by the piezoelectric chip.

It is therefore desirable to develop a neurostimulator in which a high frequency electrical signal is generated externally and transmitted through the skin causing a mechanical disturbance in an implanted piezoelectric element disposed in proximity to a nerve of interest of sufficient intensity to cause firing of an action potential in the nerve.

SUMMARY OF THE INVENTION

An aspect of the present invention is directed to piezoelectric stimulation of a nerve of interest to invoke firing of an action potential by transcutaneously applying high frequency burst packets of electrical energy.

Another aspect of the present invention is directed to piezoelectric stimulation of a nerve of interest to invoke firing of an action potential by transcutaneously applying a continuous high frequency waveform.

Still another aspect of the present invention is directed to a stimulation device including an external non-implantable transmitting device powered by a power source and generating an electrical waveform signal. A surface electrode applies the generated electrical waveform signal transcutaneously An implantable piezoelectric element receives the applied electrical waveform signal generated transcutaneously and, in turn, causes mechanical deformation resulting in mechanical vibration of the implantable piezoelectric element sufficient to stimulate a predetermined body part such as the stimulation and firing of an action potential in a nerve.

Yet another aspect of the present invention is directed to a method for stimulating a predetermined body part such as a nerve using a device in accordance with the preceding paragraph. A piezoelectric element is implanted proximate the predetermined body part. An electrical waveform signal is generated using an external non-implantable transmitting device powered by a power source. The generated electrical waveform signal is applied transcutaneously through skin via a surface electrode. A piezoelectric element implanted proximate the predetermined body part receives the applied electrical waveform signal generated transcutaneously causing it mechanically to deform resulting in mechanical vibration of the piezoelectric element sufficient to stimulate the predetermined body part.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
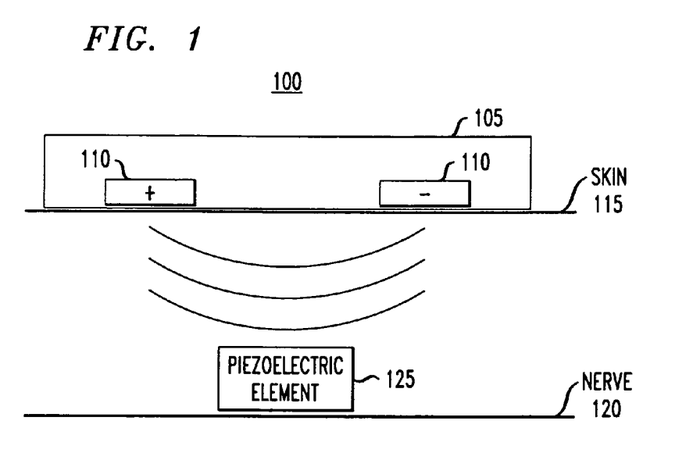
FIG. 1 depicts an exemplary schematic illustration of a piezoelectric neurostimulator in accordance with the present invention.

The present invention is directed to a neurostimulator for precise deep nerve stimulation from the surface of the skin in a minimally invasive manner. An exemplary neurostimulator 100 in accordance with the present invention is shown in FIG. 1. Neurostimulator 100 includes an external non-implantable transmitting device 105 preferably in the form of a transdermal patch or the like that is removably adhered to the skin 115 such as by using an adhesive. An electrical waveform signal generated by the transmitting device 105 and transmitted through the skin is applied across a mechanical element 125 such as a piezoelectric element disposed proximate a desired or intended nerve of interest 120 to be stimulated. Piezoelectric element 125 is comprised of a piezoelectric material that has the ability to resonate. The piezoelectric element 125 is made from a biocompatible material and/or encased in a biocompatible coating. Examples of such piezoelectric materials include natural crystals such as quartz or topaz, as well as other naturally occurring materials such as bone, ceramics with perovskite or tungsten-bronze structures. The piezoelectric element may be disposed either in direct or indirect contact with the nerve of interest. In the latter case, stimulation of the nerve of interest may be achieved indirectly by positioning the piezoelectric element in a biological volume conducting medium so that the surfaces of the material contact the fluid, whereby the generated pressure waves in the medium can be significant and sufficient to stimulate compound action potential in nerve fibers. Biological volume conducting media in this context could be muscle or fat (with extracellular fluid) adjacent to the nerve of interest. Since the volume conducting medium envelopes the nerve of interest the medium vibrates with the vibration/resonance of the piezoelectric element resulting in the firing of an action potential in the nerve without direct contact.

In one specific embodiment of a piezoelectric element adapted for use implantable in the human body, the piezoelectric element is made of a piece of quartz having a thickness of approximately 100 µm, a width of approximately 1 mm and a length of approximately 10 mm. A piezoelectric element of such dimensions may be implanted into a patient using a conventional 16 gauge needle. The dimensions of the piezoelectric element may be modified, as desired, depending on many factors such as its method of implantation into the body.

Figure 4A:
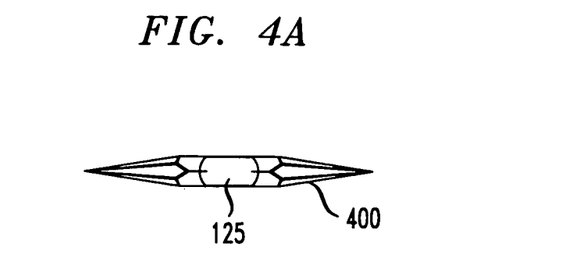
FIGS. 4A & 4B are illustrations of an exemplary implantable piezoelectric element within a cage in its non-expanded and expanded states, respectively.
Figure 4B:
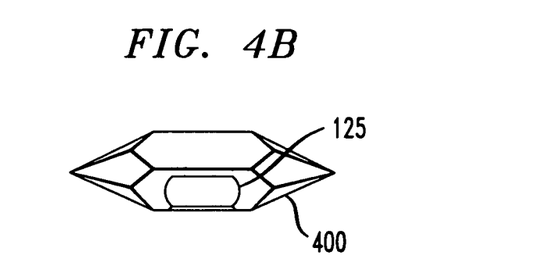

Piezoelectric element 125 may be surrounded by a housing 400 or cage as illustrated in greater detail in FIGS. 4A & 4B. In a preferred embodiment housing 400 is a collapsible cage made of a suitable metal such as Nitinol, stainless steel, a titanium alloy, or a biocompatible polymer such as polypropylene or polyethylene teraphthalate. The collapsible cage is advantageous in that it can exist in a collapsed state shown in FIG. 4A that is sufficiently small in dimension to allow insertion through an opening into the body. Once inserted into the body, as described further below, the cage assumes an expanded state shown in FIG. 4B which has a size sufficiently large to prevent it from passing out through the opening from which it was inserted. Housing or cage 400 automatically returns to its expanded state (FIG. 4B) when an external compression force is removed. Piezoelectric element 125 can be mechanically affixed to the housing or cage 400 in any suitable manner, such as by using a biocompatible adhesive.

In another embodiment, the expandable cage may be made of an absorbable material such as Ethisorb® (an absorbable synthetic composite made from polyglactin and polydioxanon) from Ethicon, Inc. of Somerville, N.J., or a combination of absorbable and non-absorbable materials. The absorbable material would preferably dissolve after a predetermined period of time so that the implantable piezoelectric element could be expelled from the body in a non-invasive manner.

Figure 5:
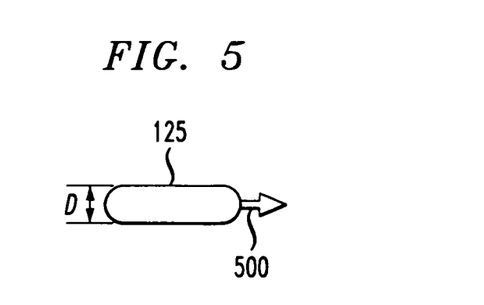
FIG. 5 is an illustration of an exemplary implantable piezoelectric element with a securing projection.

As an alternative to the collapsible cage described above, the housing may have a stable structure rather than a collapsible structure that itself has an outer diameter (D) that is smaller than the diameter of an opening in the body to allow insertion therethrough, as shown in FIG. 5. The housing may further have one or more projections 500, such as screw threads, barbs, hooks or the like, extending outwardly therefrom that can be attached to the sidewall of an organ, tissue or other internal physiological structure by being pushed or driven therein. In yet other alternate embodiments, the implantable piezoelectric element 125 could be sutured to an organ, tissue or other internal physiological structure, or adhered thereto using a suitable biocompatible adhesive.

During implantation of the piezoelectric element 125, the collapsible cage 400 is compressed and loaded into a single or multi-lumen catheter for delivery and placement at a desired nerve of interest. The catheter may be any catheter such as a Foley catheter. Fluroroscopy, ultrasound or other similar technology known to those skilled in the art may be used to aid in delivery and placement of the implantable piezoelectric element 125. If a multi-lumen catheter is used, other lumens may be used to provide an access for visualization, or monitor a physiological state of the body while placing the implantable piezoelectric element 125. An expulsion element such as a push rod or the like is inserted into the primary lumen behind, the housing 400 enclosing the piezoelectric element 125, and once the distal end of the catheter is properly positioned within the body, the expulsion element is moved toward the distal end of the catheter to thereby expel the piezoelectric element 125 enclosed in the housing 400 from the distal end of the catheter and into the body. As the implantable piezoelectric element 125 exits the catheter, the collapsible cage 400 is no longer restrained in its collapsed state, and automatically returns to its fully expanded state. Although use of a catheter is described, other suitable implantation methods may also be used, such as placement via, the working channel in a cystoscope or similar surgical tool, or placement via laparoscopic or open surgical methods. Once deployed within the body, the expandable cage is dimensioned to prevent the device from passing out from the body.

As mentioned above, alternate embodiments of the piezoelectric element 125 that do not employ a cage or housing may also be suitable, such as that shown in FIG. 5. The method of implantation of such devices would be similar to that described above, with the expulsion element within the catheter being used to drive the projecting element 500 so that it is anchored in an organ, tissue or internal physiological structure in the body. Other mechanisms for securing (e.g., barbs, hooks, anchors, projections, sutures, adhesives) the piezoelectric element 125 to an internal physiological structure thereby prohibiting its migration may be used Piezoelectric element 125 may be constructed using pieces of quartz of various sizes, as desired. The larger the volume of the piezoelectric element, the greater the vibration that can be generated. Selection of the material, structure and dimensions of the piezoelectric element is designed to achieve the desired resonance frequency required to stimulate the nerve of interest and trigger firing of an action potential. Application of an electrical field generated transcutaneously causes mechanical deformation (e.g., alternating stress) in the piezoelectric material causing it to vibrate or resonate. The vibration frequency is chosen to be the resonant frequency of the block, typically in the range of approximately 100 kHz to approximately 1 MHZ. The piezoelectric element vibrates/resonates mechanically due to the piezoelectric effect. The resulting vibration triggers an action potential either directly (piezo element in contact with the nerve) or indirectly (piezo element causes vibration of muscle/fat/fluid which encompasses nerve). Piezoelectric element 125 is designed so that it has a predetermined resonant frequency so as to trigger the firing of an action potential in the nerve of interest.

Nerves are stimulated and action potentials are generated by low frequency waveforms in the range of approximately 1 Hz-approximately 40 Hz. For example, the pudendal nerve is stimulated by a low frequency signal on the order of approximately 10 Hz-approximately 40 Hz. However, in order to stimulate such a nerve transdermally from the surface of the skin, an external signal generator must produce a high frequency waveform in the range of approximately 100 kHz-approximately 1 MHz in order to overcome the impedance of the skin and tissue so as to provide the necessary intensity of the stimulus to cause firing of the action potential for the nerve of interest. Such high frequency waveforms cannot be employed to directly stimulate a nerve since they do not respond to such high frequency signals.

Figure 2:
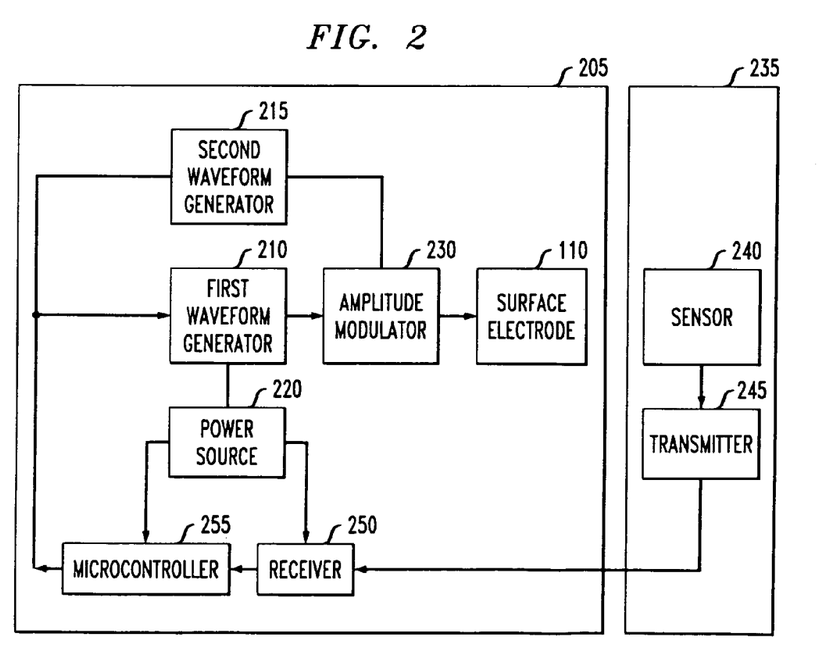
FIG. 2 is an exemplary schematic illustration of a transdermal transmission device in accordance with an embodiment of the present invention for generating a high frequency burst packet.
Figure 3A:
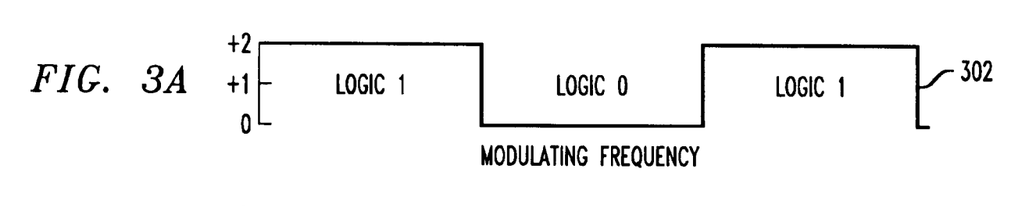
FIGS. 3A-3C are illustrative waveforms generated by the device in FIG. 2.
Figure 3B:
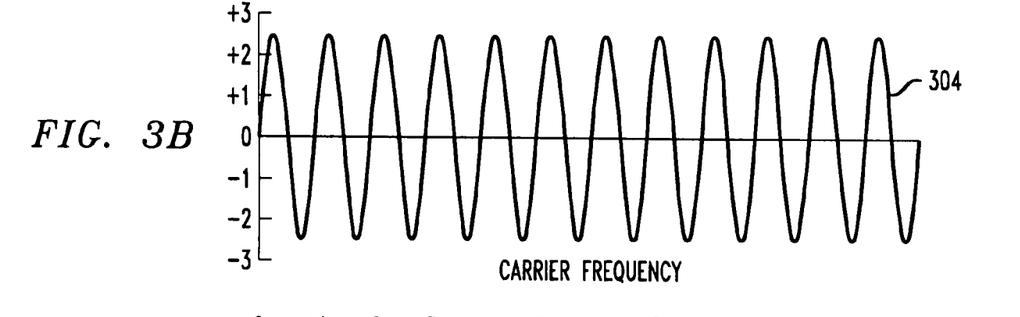
Figure 3C:
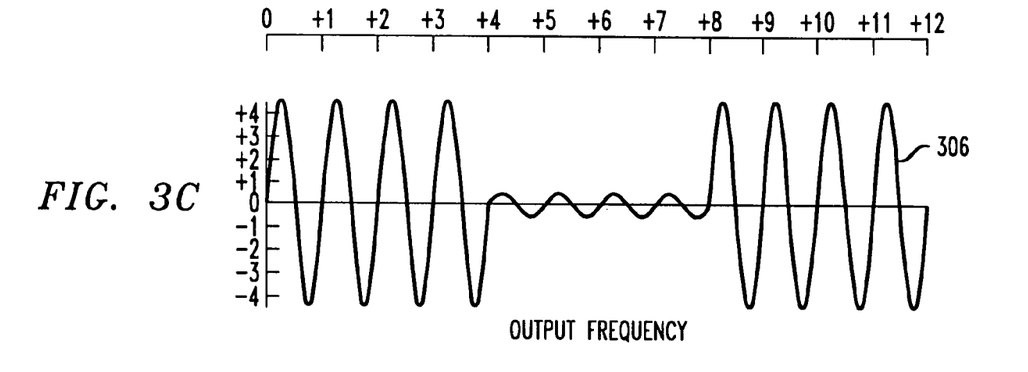

Taking such competing constraints into consideration, an action potential may be triggered in a nerve of interest with the transmitting device 105 in FIG. 1 generating either a high frequency burst packet or a high frequency continuous waveform. In a first embodiment in accordance with the present invention the transmitting device 105 generates high frequency burst packets using a transdermal signal transmission device, as disclosed in U.S. patent application Ser. No. 11/146,522, filed on Jun. 7, 2005, entitled "System and Method for Nerve Stimulation" (U.S. Patent Application Publication 2005/0277998) and assigned to the same entity as the present invention, which is herein incorporated by reference in its entirety. FIG. 2 is an exemplary embodiment of a transdermal signal transmission device 205 as the transmitting device 105 in FIG. 1 for generating high frequency burst packets. Transdermal signal transmission device 205 includes a power source 220 such as a lithium ion film battery by CYMBETT™ Corp. of Elk River, Minn., model number CPF141490L, and two waveform generators 210, 215 that are electrically coupled to and powered by the power source 220. Waveform generators 210, 215 may be of any suitable type, such as those sold by Texas Instruments of Dallas, Tex. under model number NE555. A first waveform generator 210 generates a first waveform or signal having a predetermined frequency known to stimulate a nerve of interest in the body. As indicated above, nerves are stimulated by low frequency signals. For example, the pudendal nerve is stimulated at frequencies in the range of approximately 10 Hz-approximately 40 Hz. However, such a low frequency signal applied to the skin, in and of itself, cannot pass through body tissue to reach a deep nerve with sufficient current intensity to trigger firing of an action potential. Thus, the second waveform generator 215 is provided to generate a carrier waveform, which is received with the first waveform as input to an amplitude modulator 230, such as an On-Semi MC1496 modulator by Texas Instruments. An illustrative example of the waveforms is shown in FIGS. 3A and 3B, wherein the first waveform produced by the first waveform generator 210 is a square wave having a frequency of approximately 10 Hz-approximately 40 Hz, and the second waveform produced by the second waveform generator 215 is a sinusoidal signal having a frequency in the range of approximately 10 Hz-approximately 400 kHz. Multiplying the second waveform (carrier waveform) 304 by the first waveform 302 results in a modulated waveform or output signal 306 having generally the configuration shown in FIG. 3C. The modulated signal 306 matches the resonant frequency of the piezoelectric element to produce mechanical vibration sufficient to stimulate the target nerve of interest and fire the action potential.

The modulated signal 306 is provided to an appropriate surface electrode 110, such as DURA-STICK Self Adhesive Electrodes from Chattanooga Group, Inc. of Hixson, Tenn., that applies the modulated waveform transcutaneously through the skin 115. Surface electrode 110 is depicted by a single block, however, it represents more than one physical structure, as shown in FIG. 1. The use of the modulated signal enables transmission of the waveform through physiological tissue due to the high frequency nature of the second waveform 304, yet allows it to be detected (and responded to) by the physiological target of interest due to the low frequency envelope of the modulated signal 306. These high frequency packets cause the piezoelectric element 125 to mechanically resonate. The individual burst packets are comprised of the high frequency carrier waveform in the frequency range of approximately 100 kHz-approximately 1 MHz. As previously noted above, nerves are stimulated and action potential are generated by low frequency waveforms in the range of approximately 1 Hz-approximately 40 Hz. Accordingly, the nerve of interest will only respond to the leading edge (e.g., representing a predetermined duration) of an individual burst packet due to the high frequency of the packet. In the example shown in FIGS. 3A-3C, packets arrive approximately every approximately 10 Hz-approximately 40 Hz. Thus, the nerve of interest responds to only the leading edge of each packet.

The above-described signal transmission device 205 may further include a biofeedback mechanism to create a closed-loop system and provide a system wherein nerve stimulation is selective, that is, applied only when necessary as opposed to constantly. One or more biofeedback devices 235 are preferably implanted within the body. Each biofeedback device 235 preferably includes at least one sensor 240 for monitoring, detecting or sensing a parameter such as a bio-physiological property, and a data transmission device 245 that transmits data or information gathered by the sensor back outside the body to be further processed as described more fully below.

Transdermal signal transmission device 205 may include a microcontroller or microprocessor 255 and a receiving device 250 such as a MAX1472 from Maxim Semiconductors of Sunnyvale, Calif., that is electrically coupled to and powered by the power source 220. Data from one or more of the biofeedback devices 235 is received by receiving device 250 and transmitted to the microcontroller 255. Communication from the transmitter 245 to a receiver 250 is depicted in FIG. 2 by a wired connection, however, any type of communication interface is contemplated and within the intended scope of the invention including a wireless link. Microcontroller 255 is programmed to analyze the data, and based thereon control the input data to the first and second waveform generators 210, 215 so as to control signal transmission by the transdermal signal transmission device 205. For example, the biofeedback device 235 may be a pressure sensor 240 that is implanted within the bladder. Pressure measured within the bladder over time is indicative of the existence and magnitude of bladder contractions. When such pressure measurements indicate spastic bladder muscle activity (as compared to normal bladder contractions which will result in a slow and steady rise of pressure within the bladder), a feedback signal can be communicated from the transmitter 245 to the receiving device 250 and subsequently to the microcontroller 255. Based on receipt of this signal, the microcontroller 255 will, via control of the waveform generators 210, 215, cause the electrodes 110 to transmit the modulated signal. Receipt of the modulated electrical stimulus signal across the mechanical device 125 will cause it to vibrate and stimulate the pudendal nerve.

Thus far a high frequency burst packet has been described as being produced by the transmitting device 105 using the transdermal signal transmission device 205 shown in FIG. 2. In a second embodiment shown in FIG. 6, signal transmitting device 605 generates a high frequency continuous waveform, rather than a high frequency burst packet.

Figure 6:
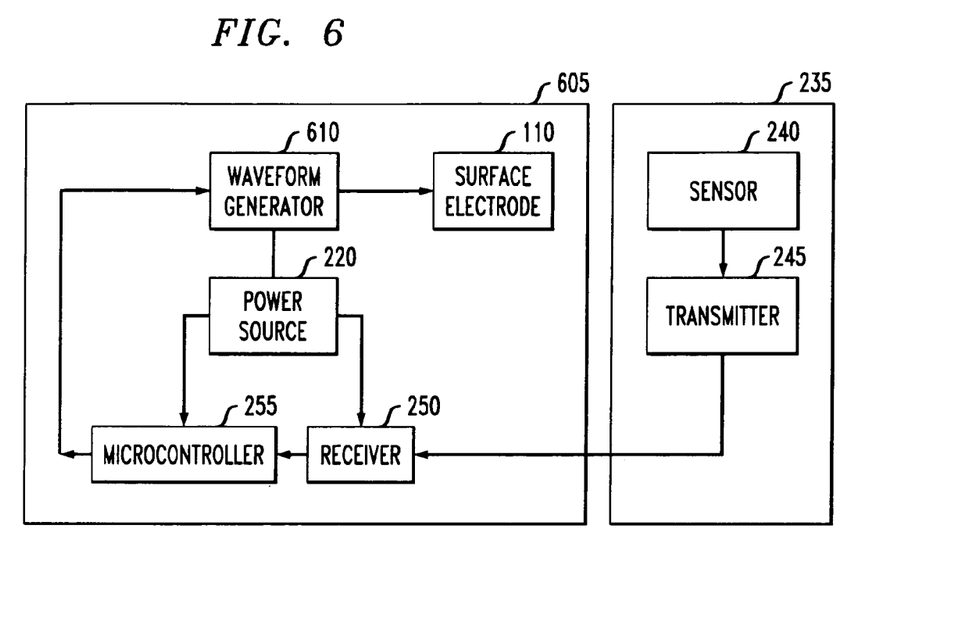
FIG. 6 is an exemplary schematic illustration of a signal transmitting device in accordance with another embodiment of the present invention for generating a high frequency continuous waveform.
Figure 7:
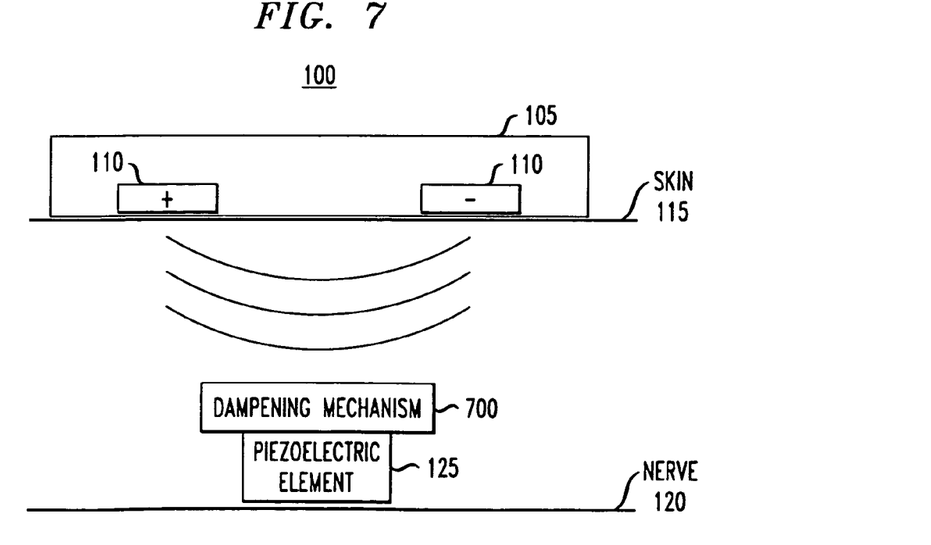
FIG. 7 depicts another exemplary schematic illustration of a piezoelectric neurostimulator in accordance with the present invention including a dampening mechanism.

Signal transmitting device 605 in accordance with this second embodiment differs from the transdermal signal transmission device 205 of FIG. 2 in that only a single waveform generator 610 is employed for generating a continuous high frequency waveform (e.g., at approximately 100 kHz-approximately 1 MHz), rather than modulated high frequency burst packets. As previously mentioned, however, nerves typically require a relatively low frequency to trigger firing of the action potential. Accordingly, application of such a high frequency continuous waveform, even taking into consideration any degradation in intensity due to tissue impedance, may still be too high to trigger firing of the action potential of the target nerve of interest. Accordingly, the resonant frequency of the mechanical device may have to be shifted downward to a lower frequency (e.g., to approximately 1 Hz-approximately 40 Hz) that the nerve of interest responds to trigger an action potential by employing a dampening or suppression mechanism 700 such as a spring or a cantilever whereby the resonant frequency depends on the length of the cantilever edge, as shown in FIG. 7. The longer the mechanical element the slower the oscillations or resonant frequency. Alternatively, or in combination therewith, the mechanical element may be encapsulated in a fluid such that the fluid resistance reduces, dampens or suppresses the number of oscillations or vibrations to a desired lower resonant frequency. Other conventional dampening or suppression techniques for downshifting the resonant frequency may be used instead of, or in combination with, any of the techniques described herein in order to realize a desired resonant frequency necessary for triggering of an action potential in a target nerve of interest.

This translation of energy from a high frequency to a low frequency signal may be achieved by restricting the resonance in only a single direction and is illustrated by way of the following example employing a cantilever.

Referring to equation (1) below, the frequency of an electric field equals the harmonic order (n) multiplied by the frequency constant (in one direction—assume in the vertical direction) of a material, divided by the thickness of a crystal, for example, quartz. The harmonic constant of quartz is 2870 kHz-mm. In order for the quartz crystal to be able to absorb the incoming resonance at 210 kHz the frequency has to be translated into a low frequency resonance of approximately 40 Hz, and requires that the movement be restricted to only the vertical direction with the length of the crystal much longer than its thickness. The specific dimensions of the crystal are calculated as follows:

$$F_x = nk_x/t \qquad \text{[Equation 1]}$$

where $F_x$ is the frequency of the electric field in one direction (in this case the x direction), n is the harmonic order,
$k_x$ is the frequency constant in the x direction (in this case for quartz listed above), and
t is the thickness of the crystal.

Using our example of quartz and 210 kHz for the desired frequency of the electric field:

$$F_x = (1) 2870 \text{ kHz-mm}/x = 210 \text{ kHz},$$

where the harmonic order (n) is assumed to be 1 for fundamental mode, and x is the thickness of the crystal.

As stated above, assuming that the length is much longer than the thickness, for instance, the length is 100 times the thickness, solving the equation above would result in a crystal 1367 mm in length and 13.67 mm in thickness, or height. This size crystal can be used as a cantilever, or dampening element. The crystal may be scaled down to a more practical size for implantation into the human body such as a length of 10 mm and a width of 100 μm.

This example quartz crystal still needs to translate the high frequency into low frequency resonance so the nerve will be stimulated. Resonant frequency is defined as follows:

$$f = \frac{1}{2\pi}\left(\frac{t}{L^2}\right)\sqrt{\frac{E}{\rho}}$$

where
t is the thickness,
L is the length,
E is Young's Modulus, and
ρ is the density.

The Young's Modulus of quartz is 71.7 GPa, and the density of quartz is 2.66 g/cm³.

It is assumed that the cantilever will reach resonance when the base of the crystal moves at 210 kHz. In order to dampen that frequency so that the end of the cantilever will resonate at 40 Hz, a damping spring is used.

By using a spring with the correct spring constant, the resonant frequency is reduced from 210 kHz to 40 Hz, which is within a specified range required for triggering firing of an action potential.

It is to be noted that in either embodiment (e.g., high frequency burst packets or high frequency continuous waveform) the biofeedback device, microcontroller and receiver may be eliminated wherein the signal generated by the transmitting device remains continuous rather than being controlled or adjusted based on any feedback data.

Piezoelectric devices allow for specific targeting of a nerve to be stimulated. Moreover, if multiple piezoelectric devices are utilized, stimulation may be selective targeting one or more of the mechanical devices at different times. In addition, the use of multiple piezoelectric devices provides the enhanced flexibility of designing each device to have the same or different resonant frequencies, as desired. By way of example only, the present invention has been described with respect to stimulation of a nerve of interest, however, stimulation of any body part is contemplated and within the intended scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A stimulation device comprising:
an external non-implantable transmitting device powered by a power source and generating an electrical waveform signal; wherein the external non-implantable transmitting device produces high frequency burst packets and comprises:
a first waveform generator for generating a first waveform having a frequency adapted to stimulate a predetermined body part, wherein the generated first waveform is itself incapable of transdermally stimulating the predetermined body part;
a second waveform generator for generating a carrier waveform having a frequency greater than that of the first waveform and adapted to puss through skin and tissue to the predetermined body part, the frequency of the generated carrier waveform is capable of reaching the predetermined body part but is itself incapable of electrically stimulating the predetermined body part;
an amplitude modulation device electrically coupled to the first and second waveform generators and configured to multiply the carrier waveform and the first waveform and producing a modulated waveform adapted to transdermally electrically stimulate the predetermined body part, the modulated waveform maintains the amplitude and frequency information of the first waveform and carrier waveform; a surface electrode electrically coupled to the modulation device applying the modulated waveform transcutaneously;
a surface electrode applying the generated electrical waveform signal transcutaneously; and
an implantable piezoelectric element receiving the applied electrical waveform signal generated transcutaneously and causing mechanical deformation resulting in mechanical vibration of the implantable piezoelectric element sufficient to stimulate the predetermined body part.

2. The stimulation device in accordance with claim 1, wherein the predetermined body part is a nerve and the mechanical vibration of the implantable piezoelectric element is sufficient to fire an action potential.

3. The stimulation device in accordance with claim 1, wherein the piezoelectric element is in direct contact with the predetermined body part.

4. The stimulation device in accordance with claim 1, wherein the piezoelectric element is in indirect contact with the predetermined body part via a biological volume conducting medium including at least one of muscle, fat or extracellular fluid.

5. The stimulation device in accordance with claim 2, wherein the external non-implantable transmitting device produces a high frequency continuous waveform and the stimulation device further comprises a dampening mechanism including one of a spring, cantilever or fluid encompassing the piezoelectric element for downshifting, a resonant frequency of the piezoelectric element.

6. The stimulation device in accordance with claim 5, wherein the high frequency continuous waveform is within the range of approximately 100 kHz-approximately 1 MHz, and the resonant frequency of the piezoelectric element is downshifted to within the range of approximately 1 Hz-approximately 40 Hz.

7. The stimulation device in accordance with claim 1, wherein the modulated waveform matches a resonant frequency of the piezoelectric element to produce mechanical vibration sufficient to stimulate the predetermined body part.

8. The stimulation device in accordance with claim 7, wherein the frequency of the first waveform is within the range of approximately 1 Hz-approximately 40 Hz.

9. The stimulation device in accordance with claim 8, wherein the frequency of the carrier waveform is within the range of approximately 100 kHz-approximately 1 MHz.

10. The stimulation device in accordance with claim 1, wherein the implantable piezoelectric element is disposed within a collapsible cage.

11. A method for stimulating the predetermined body part using the stimulation device in accordance with claim 1, the method comprising the steps of:
   implanting the piezoelectric element proximate the predetermined body part;
   generating the electrical waveform signal using, the external non-implantable transmitting device powered by the power source;
   applying the generated electrical waveform signal transcutaneously through skin via the surface electrode;
   receiving the applied electrical waveform signal generated transcutaneously at the piezoelectric element implanted proximate the predetermined body part and causing mechanical deformation resulting in mechanical vibration of the piezoelectric element sufficient to stimulate the predetermined body part.

12. The method in accordance with claim 11, wherein the predetermined body part is a nerve and the mechanical vibration of the implantable piezoelectric element is sufficient to lire an action potential.

13. The method in accordance with claim 11, wherein the piezoelectric element is in direct contact with the predetermined body part.

14. The method in accordance with claim 11, wherein the piezoelectric element is disposed in a biologically volume conducting medium sufficient to impart mechanical vibrations indirectly to the predetermined body part, wherein the biological volume conducting medium is at least one of muscle, fat or extracellular fluid.

15. The method in accordance with claim 11, wherein the external non-implantable transmitting device produces a high frequency continuous waveform; and prior to being received by the piezoelectric element, further comprising the step of downshifting a resonant frequency of the piezoelectric element to a predetermined frequency for stimulating the predetermined body part.

16. The method in accordance with claim 15, wherein the high frequency continuous waveform is within the range of approximately 100 kHz-approximately 1 MHz, and the resonant frequency of the piezoelectric element is downshifted to within the range of approximately 1 Hz-approximately 40 Hz.

17. The method in accordance with claim 16, wherein the downshifting of the resonant frequency of the applied electric waveform signal is achieved using one of a spring, cantilever or fluid encompassing the piezoelectric element.

18. The method in accordance with claim 11, wherein the external non-implantable transmitting device produces high frequency burst packets produced by the following steps:
   generating using the first waveform generator said first waveform having said frequency adapted to stimulate the predetermined body part, wherein the generated first waveform is itself incapable of transdermally electrically stimulating the predetermined body part;
   generating using the second waveform generator said carrier waveform having said frequency greater than that of the first waveform and adapted to pass through skin and tissue to the predetermined body part, the generated carrier waveform is capable of reaching the predetermined body part but is itself incapable of electrically stimulating the predetermined body part;
   modulating using the amplitude modulation device electrically coupled to the first and second waveform generators for multiplying the carrier waveform by the first waveform and producing a modulated waveform adapted to transdermally electrically stimulate the redetermined body part, the surface electrode being electrically coupled to the modulation device to apply the modulated waveform transcutaneously.

19. The method in accordance with claim 18, wherein the modulated waveform matches a resonant frequency of the piezoelectric element to produce mechanical vibration sufficient to stimulate the predetermined body part.

20. The method in accordance with claim 18, wherein the frequency of the first waveform is within the range of approximately 1 Hz-approximately 40 Hz.

21. The method in accordance with claim 20, wherein the frequency of the carrier waveform is within the range of approximately 100 kHz-approximately 1 MHz.

* * * * *